United States Patent [19]
Adams et al.

[11] Patent Number: 6,013,087
[45] Date of Patent: Jan. 11, 2000

[54] IMAGE-GUIDED SURGERY SYSTEM

[75] Inventors: Ludwig W. Adams; Willem P. Van der Brug, both of Eindhoven, Netherlands; Michael Vogele, Schwabmünchen, Germany

[73] Assignee: U.S. Philips Corporation, New York, N.Y.

[21] Appl. No.: 08/937,434

[22] Filed: Sep. 25, 1997

Related U.S. Application Data

[63] Continuation-in-part of application No. 08/855,042, May 13, 1997, Pat. No. 5,817,105.

[30] Foreign Application Priority Data

Sep. 26, 1996 [EP] European Pat. Off. ............... 96202690

[51] Int. Cl.$^7$ ..................................... A61B 19/00
[52] U.S. Cl. ........................... 606/130; 606/129; 604/116
[58] Field of Search ................... 606/129, 130; 604/116

[56] References Cited

U.S. PATENT DOCUMENTS 5,186,174  2/1993  Schlondorff et al. ................ 128/653.1
5,300,080  4/1994  Clayman et al. ....................... 606/130

*Primary Examiner*—Michael Buiz
*Assistant Examiner*—Lien Ngo
*Attorney, Agent, or Firm*—Dwight H. Renfrew, Jr.; Jack D. Slobod

[57] ABSTRACT

An image-guided surgery system includes an alignment device (1) which measures the direction of a target position (2) with respect to a starting position (4). Subsequently, the alignment device (1) places one end of the surgical instrument (3) in the starting position and rotates the surgical instrument in such a manner that it is oriented along the measured direction. It is ensured that the end meanwhile remains in the starting position. The image-guided surgery system includes a system of arms (7), one end of which is provided with an alignment member (5) for supporting the surgical instrument. The alignment member is preferably a sphere provided with an opening (6) in which the surgical instrument fits.

13 Claims, 1 Drawing Sheet

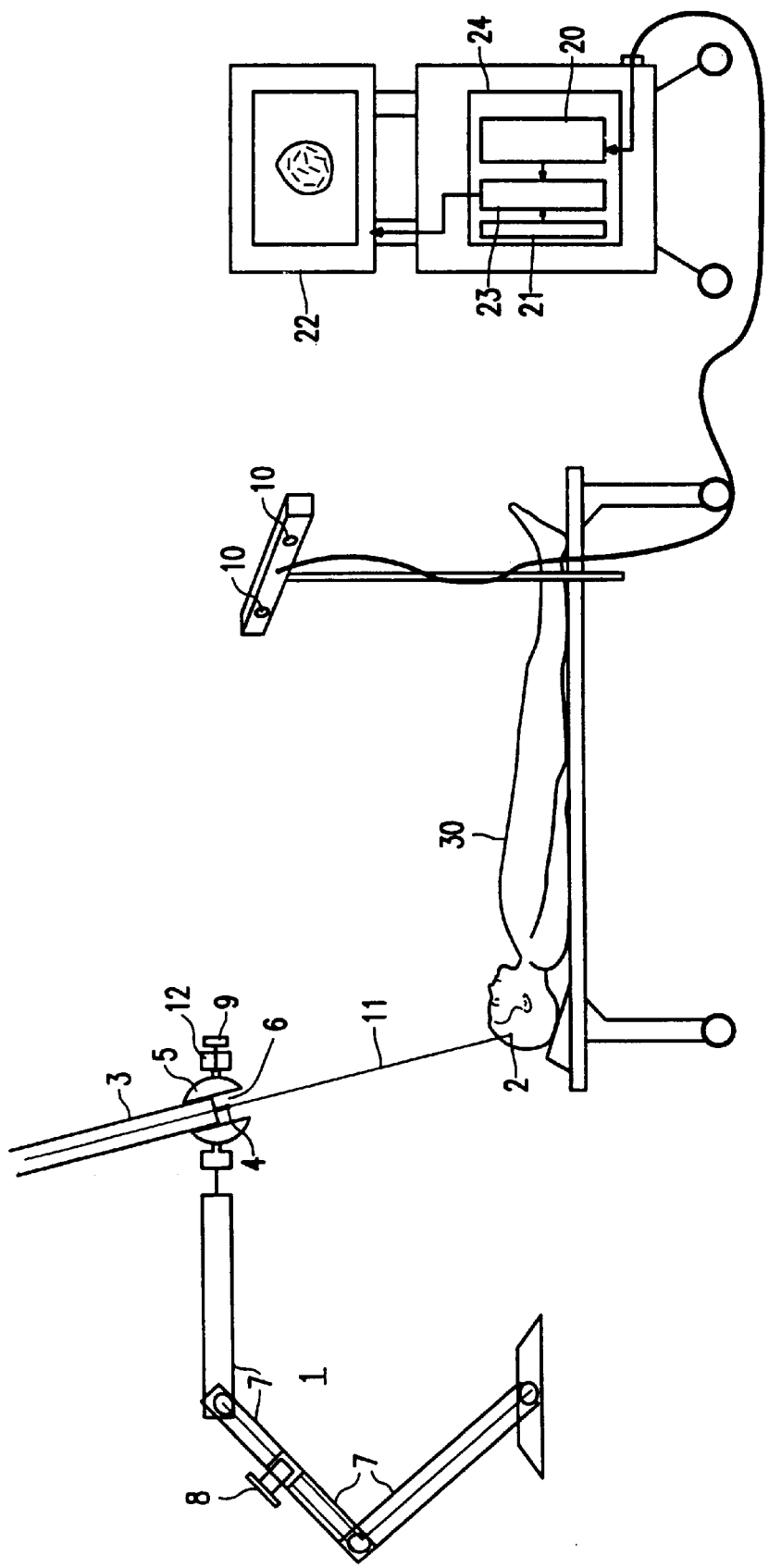

IMAGE-GUIDED SURGERY SYSTEM

This application is a continuation-in-part of U.S. Pat. No. 5,817,105, filed May 13, 1997.

BACKGROUND OF THE INVENTION

1. Field of the Invention

The invention relates to an image-guided surgery system.

2. Description of the Related Art

An image-guided surgery system of this kind is known from U.S. Pat. No. 5,186,174.

An image-guided surgery system is used to visualize a position of a surgical instrument in an operating area within the body of a patient for a surgeon during surgery. Prior to surgery images such as CT or MRI images are made of the patient. The image-guided surgery system includes a position-measuring system for measuring the position of the surgical instrument. The image-guided surgery system also includes a computer for deriving corresponding positions in a relevant image from the positions of the surgical instrument measured. During surgery the position-measuring system measures the position of the surgical instrument relative to the patient and the computer calculates the position in such a prior image which corresponds to the measured position of the surgical instrument. The prior image is then displayed on a monitor, together with the actual position of the surgical instrument. The surgeon can see the position of the surgical instrument in the operating area in the image on the monitor, without him or her seeing the surgical instrument directly. In the image displayed on the monitor the surgeon can thus see how to move the surgical instrument in the operating area without substantial risk of unnecessarily damaging tissue, and notably without risk of damaging vital parts.

An image-guided surgery system of this kind is preferably used in neuro surgery in order to show the surgeon accurately where the surgical instrument is situated in the brain during a cerebral operation.

Using the known image-guided surgery system it is difficult to position the instrument in such a manner that it is oriented in a desired direction with one end in a desired position. In order to move the instrument to the desired position and orientation, it is necessary to move it whereas at the same time the image showing the position of the surgical instrument relative to the patient must be observed so as to determine whether the desired position and orientation have been reached. It has been found that accurate positioning and orientation of the instrument require a substantial amount of training and that these operations remain time-consuming still.

SUMMARY OF THE INVENTION

It is an object of the invention to provide an image-guided surgery system in which the accurate positioning of the surgical instrument is easier and faster.

This object is achieved by means of an image-guided surgery system according to the invention which includes an alignment device for deriving a direction of a starting position relative to a target position, for arranging an end of a surgical instrument in the starting position, and for aligning a longitudinal axis of the surgical instrument along the direction derived, said end meanwhile being retained in the starting position.

The target position is a position which is usually situated in or on the body of the patient and whereto the end of the surgical instrument is to be guided during a given phase of the operation. During the operation the surgical instrument is introduced into the body of the patient via an entrance position on the surface. The target position may in some cases be the final position to be ultimately reached by the end of the surgical instrument. At the final position there is situated, for example a tumor to be removed. More generally speaking, however, the target position may be situated somewhere between the final position and the entrance position, for example, when the final position is to be reached along a curved path extending from the entrance position. The starting position is a position which, generally speaking, is situated outside the patient and in which a predetermined point of the surgical instrument, preferably the end of the surgical instrument, is positioned at the instant at which the alignment of the surgical instrument commences. The starting position is preferably chosen to be situated outside the patient and on the line which extends through the entrance position and the target position and is referred to hereinafter as the alignment line. The target position and the entrance position are selected on the basis of image information of the patient.

The computer derives the target and entrance positions from the corresponding positions in the (CT or MRI) image of the patient. The computer subsequently calculates the direction of the alignment line through the target and entrance positions and this direction is reproduced in the image so that the surgeon can choose an appropriate starting position for the relevant circumstances. Where on the alignment line the most suitable starting position is situated is dependent on the type of operation and on the associated space outside the patient in the vicinity of the entrance position. Alternatively, during the preparation of the operation a path is selected so as to extend through the body of the patient from the entrance position to the target position, the target position being reached along said path without substantial risk of damaging essential organs such as blood vessels. If such a path is determined in advance, the direction of the alignment line is that of the path at the entrance position. First the surgical instrument is positioned so that its end is situated in the selected starting position on the alignment line. It is usually not important where exactly on the alignment line the starting position is selected. The current position of the end of the surgical instrument and the alignment line are reproduced in the image, so that the end of the surgical instrument can be readily positioned in the appropriate starting position on the alignment line. Subsequently, the surgical instrument is oriented so that its longitudinal axis extends along the alignment line. Because the alignment line and the current orientation of the surgical instrument are displayed in the image, the desired orientation can be comparatively easily obtained.

Because the alignment device ensures that the end of the surgical instrument remains in the starting position when the longitudinal axis of the surgical instrument is manoeuvered along the direction derived, being the alignment line, the surgical instrument can be comparatively easily moved to the desired position and orientation. This is inter alia because only a translation is required to move the end of the surgical instrument to the starting position and subsequently only a rotation around said end is necessary so as to achieve the desired orientation of the longitudinal axis. Therefore, in the individual phases of the positioning operation only simple movements are required, that is to say only a translation and only rotation. Thus, in comparison with prior art less complex movements of the surgical instrument are required. Moreover, the surgeon need no longer pay attention that the end of the surgical instrument remains in the starting position when he/she orients the surgical instrument along the alignment line. Because the image-guided surgery system is used to derive the direction of the target position with respect to the starting position from the image, no stereotactic frame is required. Consequently, free access to the operating area is achieved.

In a preferred embodiment of an image-guided surgery system according to the invention the alignment device includes a rotatable alignment member for supporting the surgical instrument, which alignment member is arranged to lock the end of the surgical instrument in the starting position. When the alignment member locks the end of the surgical instrument in the starting position, rotation of the surgical instrument about the end remains possible. The surgical instrument is oriented along the alignment line by rotating the alignment member supporting the surgical instrument.

In a further preferred embodiment of an image-guided surgery system according to the invention, an opening is recessed in the alignment member.

The surgical instrument fits in said opening. The surgical instrument can be locked in said opening in such a manner that the end is blocked in the starting position and only rotation about said starting position remains possible.

In a further preferred embodiment of an image-guided surgery system according to the invention, the alignment member includes a spherical alignment body.

The spherical alignment body is particularly suitable for rotation around the starting position while the alignment body remains in the starting position. An approximately cylindrical hole is formed so as to extend through the spherical body. The surgical instrument fits through said hole. The surgical instrument is arranged in said hole by way of one end which is secured therein so that the end of the surgical instrument is at the center of the sphere. Subsequent rotation of the spherical body enables the surgical instrument to be oriented along the alignment line while its end remains in the starting position.

In a preferred embodiment of an image-guided surgery system according to the invention, the alignment device includes a system of arms whereto the alignment member is attached, said system of arms including a control member for adjusting the position of the alignment member and a blocking member for locking the alignment member. The system of arms comprises a number of arms which are movable relative to one another because they are coupled via one or more linking members such as hinges. Such a system of arms is known per se from the U.S. Pat. 5,186,174. The hinges can be locked so that the end of the system of arms which supports the alignment member with the surgical instrument remains in a selected position. The system of arms, notably the linking members, is locked by the control member so that the end of the surgical instrument in or on the alignment member remains in the starting position. The control member preferably comprises a single member, preferably a knob, for locking the various linking members of the system of arms in a single action. After the blocking member has locked the alignment member in a position such that the end of the surgical instrument is in the starting position, the alignment member is rotated until the surgical instrument has been oriented along the alignment line. Subsequently, the alignment member is locked so as to be immobilized. The surgical instrument can then be moved from the starting position and along the alignment line by moving it through the opening in the alignment member. The blocking member is preferably constructed also as a single knob. The system of arms and subsequently the alignment member can then be locked simply by turning two knobs in succession.

In a further preferred embodiment of an image-guided surgery system according to the invention, the alignment device is arranged to adjust a distance and to displace the surgical instrument along the alignment line over the adjusted distance.

The distance is adjusted, for example as the distance between the starting position and the entrance or target position. After the surgical instrument has been oriented along the alignment line with one end in the starting position, the end can be accurately moved to the entrance or target position. The distance to be adjusted can be calculated by the computer. To this end, the surgeon can indicate the corresponding positions of the starting position and the entrance or target position in the image.

For adjustment of the distance the alignment member includes, for example a tube which fits into the opening of the alignment member. The surgical instrument fits into said tube. The position of the tube in the alignment member can be adjusted in such a manner that when the surgical element is slid into the tube, the end of the surgical instrument reaches exactly the entrance position or the target position.

The image-guided surgery system is suitable for use for a variety of surgical operations during which the surgeon does not have a direct view of the surgical instrument within the body of the patient. Surgical operations of this kind may have a therapeutic purpose, such as the removal of tumor tissue, but surgical operations of this kind may also be used to examine the interior of the body of the patient so as to make a diagnosis. The surgical instrument is to be understood to mean a variety of instruments intended to invade the body of the patient.

These and other aspects of the invention will be apparent from and elucidated with reference to the embodiments described hereinafter.

BRIEF DESCRIPTION OF THE DRAWINGS

The Figure shows diagrammatically an image-guided surgery system according to the invention.

DETAILED DESCRIPTION OF THE PREFERRED EMBODIMENT

The image-guided surgery system includes a system of arms 1 which is provided at one end with the alignment member 5 which supports the surgical instrument 3. The system of arms includes a plurality of movable arms 7 which are rotatably coupled to one another. The image-guided surgery system also includes an optical position measuring system 10, 20 with one or more cameras 10 and a computer 20. The cameras observe the surgical instrument from different directions. To this end, the surgical instrument is provided with light or infrared emitting diodes (LEDs or IREDs) and the radiation of the diodes is detected by the cameras. On the body of the patient there are provided some marks which are reproduced in the CT or MRI image. The marks are, for example spheres of lead or tantalum which are clearly visible in a CT image. Prior to the operation the positions of the marks on the patient's body are measured by means of the image-guided surgery system. The corresponding positions in the image of the images of these marks are also taken up. On the basis of the positions of the marks on the patient and the positions of the images of the marks in the image the computer 20 derives the transformation which transforms arbitrary positions in (or in the vicinity of) the patient into corresponding positions in the image.

The computer 20 derives the position of the surgical instrument 3, and hence also the corresponding position in a CT or MRI image of the patient, from the signals supplied by the cameras 10. This CT or MRI image may be formed prior to or during the operation. The CT or MRI image can then be fetched from an image memory 21. A monitor 22 displays the relevant image in which the position of the surgical instrument is shown. Via an image processing unit 23, the relevant image from the image memory is combined with the position of the surgical instrument in the image as calculated by the computer. The computer 20, the image memory 21 and the image processing unit 23 are included in a data processor 24.

The end 4 of the surgical instrument 3 must be moved to a target position 2 in the patient 30. To this end, the relevant image is displayed on the monitor 22. The surgeon selects the target position in said image, said position being marked, for example by means of a symbol in a first color. The surgeon also selects the entrance position, being the position on the surface of the patient's body where the surgical instrument enters the body of the patient. For example, in the case of brain surgery the entrance position is situated on the skull of the patient. Furthermore, the computer calculates the direction of the alignment line extending through the target position and the entrance position. The alignment line is preferably the tangent in the entrance position to a preselected path to be followed by the surgical instrument to the final position. Using the data processor, the line corresponding to the alignment line in the image is reproduced. Furthermore, the surgeon arranges the alignment member 5, in which the surgical instrument has been fitted, in such a manner that its end is situated in a suitable starting position 4 on the alignment line 11. The optical position measuring system measures the starting position and the starting position is reproduced in the image of the patient on the monitor, for example by means of another symbol and/or in a different color. Thus, actually the alignment line is reproduced in the image with the starting and target positions and the current position and orientation of the surgical instrument 3.

The surgical instrument 3 is arranged in the opening 6 in the alignment member. The alignment member preferably includes an alignment body 5 in the form of a sphere. The sphere is rotatable in a bearing 12 and can be locked therein by means of a blocking member 9. A hole 6 is drilled through the center of the sphere 5, the surgical instrument fitting in said hole in such a manner that its end comes to rest at the center of the sphere 5. By moving the sphere by means of the system of arms, the end of the surgical instrument 3 is moved to the starting position 4 in which the orientation of the surgical element is not yet relevant and hence the end of the surgical instrument 3 can be easily moved to the starting position 4 on the basis of the image displayed on the monitor. Using the control member 8, in this case consisting of a knob, the system of arms is locked while the end of the surgical instrument is in the starting position 4. Subsequently, the surgical instrument can also be rotated about the starting position 4; the surgical instrument 3, fitting the hole 6, then rotates the sphere 5, but the end of the surgical instrument remains at the center of the sphere 5 and in the starting position 4. The longitudinal axis of the surgical instrument can then be readily aligned along the alignment line on the basis of the image displayed on the monitor. The end of the surgical instrument then remains exactly in the starting position 4. When the sphere, together with the surgical instrument, has been rotated to the correct position, it is locked by means of the blocking member, again being a knob 9. The surgical instrument may then be slid through the hole and the end of the surgical instrument will then accurately move along the alignment line from the starting position 4, via the entrance position, to the target position 2.

We claim:

1. An image-guided surgery system comprising:
   means for determining a current position and orientation of a surgical instrument
   means for (i) deriving a direction of a starting position of the surgical instrument relative to a target position from corresponding positions in one or more images of a patient, and for (ii) displaying the derived direction and the current position and orientation of the surgical instrument in the one or more images, and
   an alignment device for arranging an end of the surgical instrument in the starting position and aligning a longitudinal axis of the surgical instrument along the direction derived while retaining said end in the starting position.

2. An image-guided surgery system comprising:
   means for deriving a direction of a starting position a surgical instrument relative to a target position from corresponding positions in one or more images of a patient, and
   an alignment device for arranging an end of the surgical instrument in the starting position and aligning a longitudinal axis of the surgical instrument along the direction derived while retaining said end in the starting position, wherein the alignment device comprises a rotatable alignment member for supporting the surgical instrument, of said rotatable alignment member for locking the end of the surgical instrument in the starting position while permitting alignment of the longitudinal axis of the surgical instrument.

3. An image-guided surgery system as claimed in claim 2 wherein the rotatable alignment member comprises a spherical alignment body having a recessed opening into which the surgical instrument fits so that the end of the surgical instrument is at the center of the spherical alignment body.

4. An image-guided surgery system as claimed in claim 2 wherein the alignment device includes a system of arms to which the rotatable alignment member is attached, and which includes a control member for locking the position of the rotatable alignment member, and a blocking member for separately locking the alignment of the rotatable alignment member.

5. An image-guided surgery system as claimed in claim 2, in which the alignment device is arranged to adjust a distance, and to permit displacement the surgical instrument along the derived direction over the adjusted distance.

6. An image-guided surgery system as claimed in claim 3 wherein the alignment device includes a system of arms to which the rotatable alignment member is attached, and which includes a control member for locking the position of the rotatable alignment member, and a blocking member for separately locking the alignment of the rotatable alignment member.

7. The system of claim 3 wherein the alignment device is arranged to adjust a distance and to permit displacement the surgical instrument along the derived direction over the adjusted distance.

8. The system of claim 4 wherein the rotatable alignment member comprises a spherical alignment body having a recessed opening into which the surgical instrument fits so that the end of the surgical instrument is at the center of the spherical alignment body.

9. The system of claim 4 wherein the alignment device is arranged to adjust a distance and to permit displacement the surgical instrument along the derived direction over the adjusted distance.

10. A method of image guided surgery comprising:

deriving a direction of a starting position of a surgical instrument relative to a target position from corresponding positions in one or more images of a patient displaying the derived direction along with a current position of an end and a current orientation of the surgical instrument, filling the end of the surgical instrument in a rotatable alignment member, positioning the rotatable alignment member so that the end of the surgical instrument is in the starting position, locking the rotatable alignment member so that the end of the surgical instrument is retained in the starting position, and rotating the rotatable alignment member so that a longitudinal axis of the surgical instruments is aligned along the direction derived while retaining said end in the starting position.

11. The device of claim 2 further comprising means for displaying the derived direction along with a current position of the end and a current orientation of the surgical instrument.

12. The device of claim 2 wherein the means for deriving comprise a computer and an image memory.

13. The device of claim 2 wherein the means for deriving comprise a optical position measuring system.

* * * * *